(12) United States Patent
Sampathkumaran

(10) Patent No.: US 9,710,612 B2
(45) Date of Patent: Jul. 18, 2017

(54) COMBINING SIGNAL INFORMATION FROM SHOES AND SPORTS RACKET

(71) Applicant: Sony Corporation, Tokyo (JP)

(72) Inventor: Sriram Sampathkumaran, San Diego, CA (US)

(73) Assignee: Sony Corporation, Tokyo (JP)

( * ) Notice: Subject to any disclaimer, the term of this patent is extended or adjusted under 35 U.S.C. 154(b) by 265 days.

(21) Appl. No.: 14/269,499

(22) Filed: May 5, 2014

(65) Prior Publication Data

US 2015/0314164 A1 Nov. 5, 2015

(51) Int. Cl.
| | |
|---|---|
| G06F 19/00 | (2011.01) |
| A61B 5/00 | (2006.01) |
| G06K 9/00 | (2006.01) |
| G09B 19/00 | (2006.01) |
| A63B 24/00 | (2006.01) |
| A63B 71/06 | (2006.01) |
| A63B 69/38 | (2006.01) |

(52) U.S. Cl.
CPC ........ *G06F 19/3481* (2013.01); *A61B 5/6807* (2013.01); *A61B 5/6895* (2013.01); *A63B 24/0006* (2013.01); *A63B 24/0062* (2013.01); *A63B 69/38* (2013.01); *A63B 71/0622* (2013.01); *G06K 9/00342* (2013.01); *G09B 19/0038* (2013.01); *A61B 2505/09* (2013.01); *A61B 2562/0219* (2013.01); *A63B 2220/56* (2013.01); *A63B 2220/803* (2013.01); *A63B 2220/833* (2013.01); *A63B 2220/836* (2013.01)

(58) Field of Classification Search
CPC ...... A63B 2220/0062; A63B 2220/833; A63B 2220/836; A63B 69/38
See application file for complete search history.

(56) References Cited

U.S. PATENT DOCUMENTS

| | | |
|---|---|---|
| 5,059,944 A | 10/1991 | Carmona |
| 8,262,517 B2 | 9/2012 | Balasubramanyan |
| 8,465,376 B2 | 6/2013 | Bentley |
| 2003/0216228 A1 | 11/2003 | Rast |
| 2005/0239583 A1* | 10/2005 | Damen .............. A63B 24/0021 473/516 |
| 2007/0197938 A1 | 8/2007 | Tyson et al. |
| 2008/0174550 A1 | 7/2008 | Laurila et al. |
| 2008/0258921 A1* | 10/2008 | Woo ..................... A61B 5/0002 340/573.1 |
| 2009/0029754 A1 | 1/2009 | Slocum et al. |
| 2010/0081116 A1 | 4/2010 | Barasch et al. |
| 2010/0281432 A1 | 11/2010 | Geisner et al. |
| 2011/0183787 A1* | 7/2011 | Schwenger ............ A63B 49/00 473/553 |

(Continued)

OTHER PUBLICATIONS

Sriram Sampathkumaran, "Using Pressure Signal from Racket to Advise Player", file history of related pending U.S. Appl. No. 14/269,681, filed May 5, 2014.

(Continued)

*Primary Examiner* — Milap Shah
*Assistant Examiner* — Robert T. Clarke, Jr.
(74) *Attorney, Agent, or Firm* — John L. Rogitz

(57) ABSTRACT

Methods and apparatus are disclosed for correlating signals from a sports racket with signals from the shoes worn by a player wielding the racket to gain insight into the player's footwork at ball striking moments.

17 Claims, 3 Drawing Sheets

(56) References Cited

U.S. PATENT DOCUMENTS

| | | |
|---|---|---|
| 2011/0230273 A1 | 9/2011 | Niegowski et al. |
| 2011/0230274 A1 | 9/2011 | Lafortune et al. |
| 2011/0230985 A1 | 9/2011 | Niegowski et al. |
| 2011/0230986 A1 | 9/2011 | Lafortune et al. |
| 2012/0004055 A1 | 1/2012 | Balasubramanyan |
| 2012/0028047 A1 | 2/2012 | Imai et al. |
| 2012/0052971 A1 | 3/2012 | Bentley |
| 2012/0052972 A1 | 3/2012 | Bentley |
| 2012/0190505 A1 | 7/2012 | Shavit et al. |
| 2013/0066588 A1 | 3/2013 | Sherry |
| 2013/0071815 A1 | 3/2013 | Hudson et al. |
| 2013/0211774 A1 | 8/2013 | Bentley et al. |
| 2013/0250118 A1* | 9/2013 | Kawakami ............. H04N 7/183 348/157 |
| 2013/0274040 A1* | 10/2013 | Coza .................. G09B 19/0038 473/570 |

OTHER PUBLICATIONS

Sriram Sampathkumaran, "Using Pressure Signal from Racket to Advise Player", related U.S. Appl. No. 14/269,681, Applicant's response to Final Office Action filed Sep. 1, 2016.
Sriram Sampathkumaran, "Using Pressure Signal From Racket to Advise Player", related U.S. Appl. No. 14/269,681, Final Office Action dated Aug. 30, 2016.
Sriram Smapathkumaran, "Using Pressure Signal from Racket to Advise Player" related pending U.S. Appl. No. 14/269,681, non-final office action dated Jun. 17, 2016.
Sriram Sampathkumaran, "Using Pressure Signal from Racket to Advise Player", related pending U.S. Appl. No. 14/269,681, applicant's response to non-final office action filed Jun. 17, 2016.

\* cited by examiner

COMBINING SIGNAL INFORMATION FROM SHOES AND SPORTS RACKET

FIELD OF THE INVENTION

The present application relates generally to combining signal information from sports shoes and sports rackets to give a player insights into his or her play.

BACKGROUND OF THE INVENTION

A computer ecosystem, or digital ecosystem, is an adaptive and distributed socio-technical system that is characterized by its sustainability, self-organization, and scalability. Inspired by environmental ecosystems, which consist of biotic and abiotic components that interact through nutrient cycles and energy flows, complete computer ecosystems consist of hardware, software, and services that in some cases may be provided by one company, such as Sony. The goal of each computer ecosystem is to provide consumers with everything that may be desired, at least in part services and/or software that may be exchanged via the Internet. Moreover, interconnectedness and sharing among elements of an ecosystem, such as applications within a computing cloud, provides consumers with increased capability to organize and access data and presents itself as the future characteristic of efficient integrative ecosystems.

Two general types of computer ecosystems exist: vertical and horizontal computer ecosystems. In the vertical approach, virtually all aspects of the ecosystem are owned and controlled by one company, and are specifically designed to seamlessly interact with one another. Horizontal ecosystems, one the other hand, integrate aspects such as hardware and software that are created by other entities into one unified ecosystem. The horizontal approach allows for greater variety of input from consumers and manufactures, increasing the capacity for novel innovations and adaptations to changing demands.

Present principles are directed to specific aspects of computer ecosystems, specifically, to permitting tennis players who are engrossed in their game during play to later correlate errors and advantages in their footwork during ball strikes to the ball strikes to advantageously gain insight into strengths and weaknesses of their game.

SUMMARY OF THE INVENTION

As understood herein, sensors have been provided in shoes to provide electrical signals representing various characteristics of the wearer's performance while wearing the shoes in, e.g., athletic endeavors. An example is given in U.S. Pat. No. 6,807,869, incorporated herein by reference. More recently, the companies Nike and Apple have teamed to provide a sensor in a so-called "Nike+" shoe that wirelessly transmits performance data to an Apple device such as an iPod (one or more of these terms are trademarks of the respective companies).

As further understood herein, during a tennis game, a player may generally be too focused on the ball and in the heat of the moment, and not have sufficient awareness of the interplay between his footwork and his strokes. Some players video themselves for later viewing but typically the player's camera must be positioned in a spot where it is least likely to get hit by the ball, therefore it has to be relatively far from the player at an angle which tends to narrow the angle of view. Also, shots at the baseline and at the net cannot be simultaneously captured. Further, the camera captures frames at thirty frames per second, which is too slow to adequately capture the stroke or the ball. Present principles recognize that if a player can obtain information from his shoes about the footwork and also stroke-related information, the two can be combined onto the same time-bar for insight.

Accordingly, a device includes at least one computer readable storage medium bearing instructions executable by a processor, and at least one processor configured for accessing the computer readable storage medium to execute the instructions to configure the processor for receiving first signals from at least one sensor on a sports racket, as well as receiving second signals from at least one sensor on a shoe worn by a player wielding the sports racket. The instructions when executed by the processor configure the processor for, based at least in part on the first and second signals, presenting an indication on at least one display.

The indication may be audible and/or visual. The presenting may be based at least in part on a synchronization of the first and second signals. The instructions when executed by the processor may configure the processor for determining a player struck an object with the racket based at least in part on signals from at least one strike sensor on the racket. In other examples, the instructions when executed by the processor configure the processor for determining a player struck an object with the racket based at least in part on signals from at least one pressure sensor on a handle of the racket. In some implementations, the instructions when executed by the processor configure the processor for determining from signals from at least one motion sensor on the racket whether a racket has been swung in clockwise or counterclockwise arc.

In example embodiments, the indication can include at least one expert evaluation. In some example implementations, the indication may include at least one timeline of shoe pressure and/or video of the player synchronized with at least one comment derived from the first and second signals.

In another aspect, a method correlating first signals from a sports racket with second signals from shoes worn by a player wielding the racket; and presenting an indication based at least in part on the first and second signals to allow the player to gain insight into the player's footwork at ball striking moments.

In another aspect, a system includes at least one shoe and at least one sensor on the shoe configured for generating first signals. The system also includes at least one racket and at least one sensor on the racket configured for generating second signals. Also, the system includes at least one computing device configured for receiving the first and second signals and outputting an indication based thereon.

The details of the present invention, both as to its structure and operation, can be best understood in reference to the accompanying drawings, in which like reference numerals refer to like parts, and in which:

DETAILED DESCRIPTION OF THE PREFERRED EMBODIMENT

Figure 1:
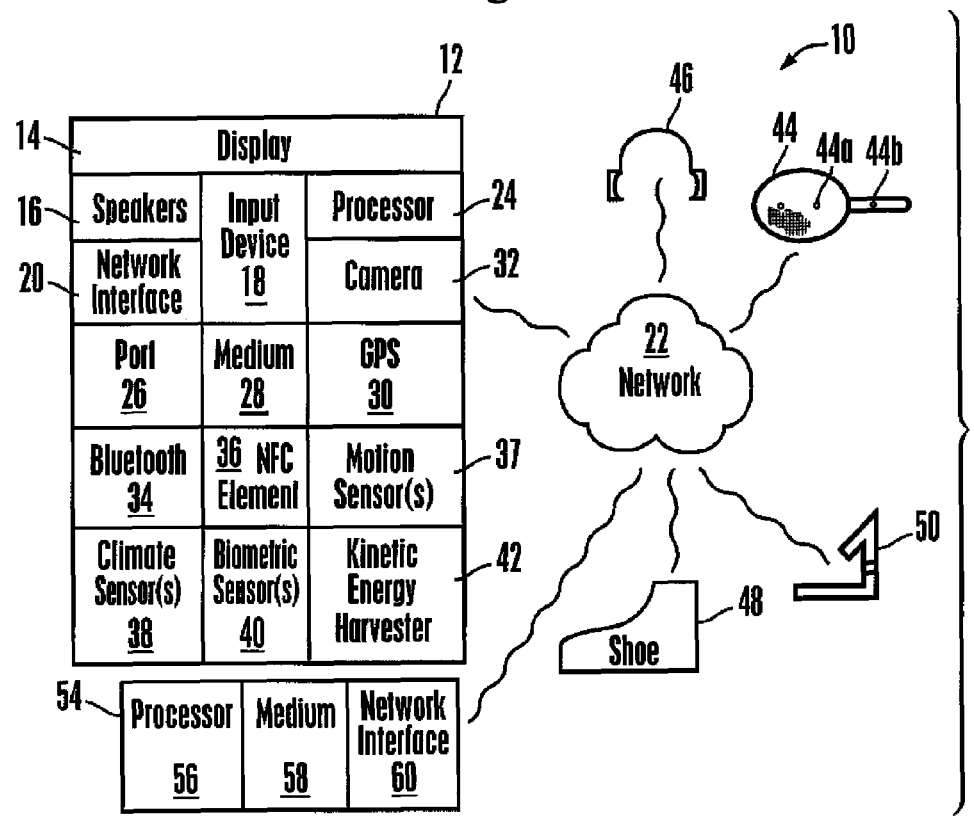
FIG. 1 is a block diagram of an example system including an example in accordance with present principles.

As set forth further below, one or more sensors such as but not limited to gyroscopes/3D-direction sensors, compasses, accelerometers, and pedometers may be engaged with tennis footwear to output signals representing the footwork of the person wearing the footwear before and after hitting the stroke. Note that footwork can include the number of steps taken before a stroke, the distance between each step, the orientation of the feet with respect to each other, etc. Footwork in the context of tennis can also include how the player positions himself with respect to an incoming ball, an analysis which requires at least one racket sensor to indicate ball strikes (strokes) to derive inferences. Pressure sensors may also be used in the shoes to sense the distribution of the player's weight so that for a particular stroke it can be indicated whether there was excess weight on one particular foot, etc. Further, this sort of data can be useful in statistical inferences to link certain types of injury or performance to a certain pressure distribution. And this can be used to prevent certain types of injury as well. For example, in soccer it is noticed that certain players are highly agile and nimble because their weight is more on their toes and they don't use their heel. This knowledge can help players to grow, and also help therapists in focusing on problem areas.

Thus, as disclosed further below, sensors are provided in shoes and other sensors are provided in the wearer's sports racket, with the sensors communicating wirelessly with a mobile device such as a tablet computer for real time processing. Or, the data from the sensors may stored and analyzed post-play. A web service may be used for the processing in case the processing is heavy or to save/backup the data.

Accordingly, in general this disclosure relates generally to computer ecosystems including aspects of consumer electronics (CE) device based user information in computer ecosystems. A system herein may include server and client components, connected over a network such that data may be exchanged between the client and server components. The client components may include one or more computing devices including portable televisions (e.g. smart TVs, Internet-enabled TVs), portable computers such as laptops and tablet computers, and other mobile devices including smart phones and additional examples discussed below. These client devices may operate with a variety of operating environments. For example, some of the client computers may employ, as examples, operating systems from Microsoft, or a Unix operating system, or operating systems produced by Apple Computer or Google. These operating environments may be used to execute one or more browsing programs, such as a browser made by Microsoft or Google or Mozilla or other browser program that can access web applications hosted by the Internet servers discussed below.

Servers may include one or more processors executing instructions that configure the servers to receive and transmit data over a network such as the Internet. Or, a client and server can be connected over a local intranet or a virtual private network.

Information may be exchanged over a network between the clients and servers. To this end and for security, servers and/or clients can include firewalls, load balancers, temporary storages, and proxies, and other network infrastructure for reliability and security. One or more servers may form an apparatus that implement methods of providing a secure community such as an online social website to network members.

As used herein, instructions refer to computer-implemented steps for processing information in the system. Instructions can be implemented in software, firmware or hardware and include any type of programmed step undertaken by components of the system.

A processor may be any conventional general purpose single- or multi-chip processor that can execute logic by means of various lines such as address lines, data lines, and control lines and registers and shift registers.

Software modules described by way of the flow charts and user interfaces herein can include various sub-routines, procedures, etc. Without limiting the disclosure, logic stated to be executed by a particular module can be redistributed to other software modules and/or combined together in a single module and/or made available in a shareable library.

Present principles described herein can be implemented as hardware, software, firmware, or combinations thereof; hence, illustrative components, blocks, modules, circuits, and steps are set forth in terms of their functionality.

Further to what has been alluded to above, logical blocks, modules, and circuits described below can be implemented or performed with a general purpose processor, a digital signal processor (DSP), a field programmable gate array (FPGA) or other programmable logic device such as an application specific integrated circuit (ASIC), discrete gate or transistor logic, discrete hardware components, or any combination thereof designed to perform the functions described herein. A processor can be implemented by a controller or state machine or a combination of computing devices.

The functions and methods described below, when implemented in software, can be written in an appropriate language such as but not limited to C# or C++, and can be stored on or transmitted through a computer-readable storage medium such as a random access memory (RAM), read-only memory (ROM), electrically erasable programmable read-only memory (EEPROM), compact disk read-only memory (CD-ROM) or other optical disk storage such as digital versatile disc (DVD), magnetic disk storage or other magnetic storage devices including removable thumb drives, etc. A connection may establish a computer-readable medium. Such connections can include, as examples, hard-wired cables including fiber optics and coaxial wires and digital subscriber line (DSL) and twisted pair wires. Such connections may include wireless communication connections including infrared and radio.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

Now specifically referring to FIG. 1, an example system 10 is shown, which may include one or more of the example devices mentioned above and described further below in accordance with present principles. The first of the example devices included in the system 10 is an example consumer electronics (CE) device 12 that may be waterproof (e.g., for use while swimming). The CE device 12 may be, e.g., a computerized Internet enabled ("smart") telephone, a tablet computer, an iPod, a notebook computer, a wearable computerized device such as e.g. computerized Internet-enabled watch, a computerized Internet-enabled bracelet, other computerized Internet-enabled devices, a computerized Internet-enabled music player, computerized Internet-enabled head phones, a computerized Internet-enabled implantable device such as an implantable skin device, etc., and even e.g. a computerized Internet-enabled television (TV). Regardless, it is to be understood that the CE device 12 is configured to undertake present principles (e.g. communicate with other CE devices to undertake present principles, execute the logic described herein, and perform any other functions and/or operations described herein).

Accordingly, to undertake such principles the CE device 12 can be established by some or all of the components shown in FIG. 1. For example, the CE device 12 can include one or more touch-enabled displays 14, one or more speakers 16 for outputting audio in accordance with present principles, and at least one additional input device 18 such as e.g. an audio receiver/microphone for e.g. entering audible commands to the CE device 12 to control the CE device 12. The example CE device 12 may also include one or more network interfaces 20 for communication over at least one network 22 such as the Internet, an WAN, an LAN, etc. under control of one or more processors 24. It is to be understood that the processor 24 controls the CE device 12 to undertake present principles, including the other elements of the CE device 12 described herein such as e.g. controlling the display 14 to present images thereon and receiving input therefrom. Furthermore, note the network interface 20 may be, e.g., a wired or wireless modem or router, or other appropriate interface such as, e.g., a wireless telephony transceiver, WiFi transceiver, etc.

In addition to the foregoing, the CE device 12 may also include one or more input ports 26 such as, e.g., a USB port to physically connect (e.g. using a wired connection) to another CE device and/or a headphone port to connect headphones to the CE device 12 for presentation of audio from the CE device 12 to a user through the headphones. The CE device 12 may further include one or more tangible computer readable storage medium 28 such as disk-based or solid state storage, it being understood that the computer readable storage medium 28 may not be a carrier wave. Also in some embodiments, the CE device 12 can include a position or location receiver such as but not limited to a GPS receiver and/or altimeter 30 that is configured to e.g. receive geographic position information from at least one satellite and provide the information to the processor 24 and/or determine an altitude at which the CE device 12 is disposed in conjunction with the processor 24. However, it is to be understood that that another suitable position receiver other than a GPS receiver and/or altimeter may be used in accordance with present principles to e.g. determine the location of the CE device 12 in e.g. all three dimensions.

Continuing the description of the CE device 12, in some embodiments the CE device 12 may include one or more cameras 32 that may be, e.g., a thermal imaging camera, a digital camera such as a webcam, and/or a camera integrated into the CE device 12 and controllable by the processor 24 to gather pictures/images and/or video in accordance with present principles. Also included on the CE device 12 may be a Bluetooth transceiver 34 and other Near Field Communication (NFC) element 36 for communication with other devices using Bluetooth and/or NFC technology, respectively. An example NFC element can be a radio frequency identification (RFID) element.

Further still, the CE device 12 may include one or more motion sensors 37 (e.g., an accelerometer, gyroscope, cyclometer, magnetic sensor, infrared (IR) motion sensors such as passive IR sensors, an optical sensor, a speed and/or cadence sensor, a gesture sensor (e.g. for sensing gesture command), etc.) providing input to the processor 24. The CE device 12 may include still other sensors such as e.g. one or more climate sensors 38 (e.g. barometers, humidity sensors, wind sensors, light sensors, temperature sensors, etc.) and/or one or more biometric sensors 40 providing input to the processor 24. In addition to the foregoing, it is noted that in some embodiments the CE device 12 may also include a kinetic energy harvester 42 to e.g. charge a battery (not shown) powering the CE device 12.

Still referring to FIG. 1, in addition to the CE device 12, the system 10 may include one or more other CE device types such as, but not limited to, a computerized sports racket 44 such as a tennis racket, badminton racket, table tennis racket, squash racket, or racquetball racket. One or more strike sensors 44a sense when the head contacts a tennis ball and one or more handle sensors 44b such as a pressure sensors embedded in a pressure-sensitive mat to sense a person's grip on the handle. A block diagram of additional components of the sports racket 44 is shown and described below.

Also, computerized Internet-enabled headphones and/or ear buds 46 may be provided, as well as computerized Internet-enabled clothing 48 such as sports shoes, an example of which is discussed further below. Moreover, a computerized Internet-enabled exercise machine 50 (e.g. a treadmill, exercise bike, elliptical machine, etc.), may be provided. It is to be understood that other CE devices included in the system 10 including those described in this paragraph may respectively include some or all of the various components described above in reference to the CE device 12 such but not limited to e.g. the biometric sensors and motion sensors described above, as well as the position receivers, cameras, input devices, and speakers also described above.

Now in reference to the afore-mentioned at least one server 54, it includes at least one processor 56, at least one tangible computer readable storage medium 58 that may not be a carrier wave such as disk-based or solid state storage, and at least one network interface 60 that, under control of the processor 56, allows for communication with the other CE devices of FIG. 1 over the network 22, and indeed may facilitate communication between servers and client devices in accordance with present principles. Note that the network interface 60 may be, e.g., a wired or wireless modem or router, WiFi transceiver, or other appropriate interface such as, e.g., a wireless telephony transceiver.

Accordingly, in some embodiments the server 54 may be an Internet server, may include and perform "cloud" functions such that the CE devices of the system 10 may access a "cloud" environment via the server 54 in example embodiments.

Figure 2:
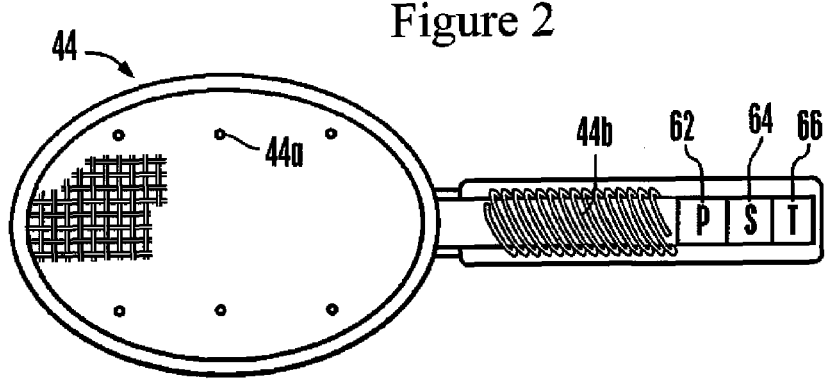
FIG. 2 is a schematic diagram of a sports racket according to present principles.

Now referring to FIG. 2, a schematic view of a sports racket 44 is shown which includes one or more strike sensors 44a and one or more handle sensors 44b. Although the strike sensors 44a are shown on the head of the racket, e.g., on the frame of the head, in some embodiments the strike sensors 44a may be on the handle. In some embodiments the strike sensors 44a may be omitted and only the handle sensor 44b used according to description below. Without limitation, the strike sensors 44a may be implemented by accelerometers, gyroscopes, force sensing resistors, etc.

In some example non-limiting embodiments the handle sensor 44*b* may be implemented by a pressure-sensitive mat such as those described in, e.g., U.S. Pat. Nos. 7,785,704 and 5,033,291, incorporated herein by reference and configured to surround the handle of the sports racket as shown, just beneath the typically leather or rubber grip of the handle. In any case, the sensors 44*a*, 44*b* communicate signals to a racket processor 62 accessing a computer storage medium 64 and wirelessly sending the signals through a wireless transceiver 66, processed as described below by the racket processor 62 or unprocessed for processing by a receiving processor.

Figure 3:
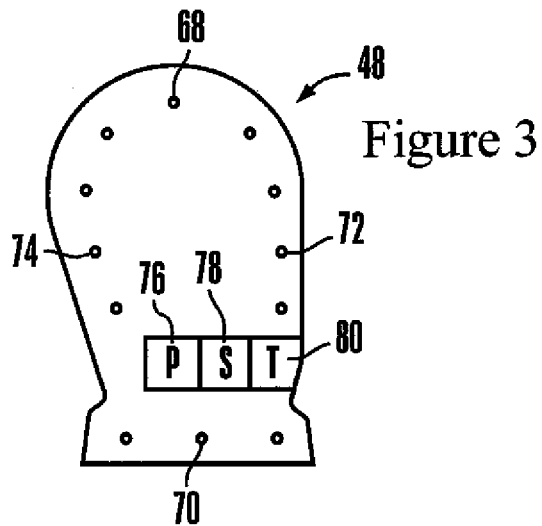
FIG. 3 is a schematic diagram of a sports shoe according to present principles.

FIG. 3 shows a schematic diagram of an example non-limiting sports shoe 48 with one or more toe pressure sensors 68, one or more heel pressure sensors 70, one or more pronation pressure sensors 72, and one or more supination pressure sensors 74 communicating respective pressure signals to a shoe processor 76 accessing a computer readable storage device 78 for wirelessly transmitting pressure signals through a wireless transceiver 80.

The shoe sensor signals and racket sensor signals may be sent to the CE device 12 via short-range communications such as NFC or Bluetooth or via the network 22 via, e.g., using Wi-Fi. The signals are time-stamped by their originating devices and/or receiving device(s) for synchronization purposes to be shortly disclosed.

Figure 4:
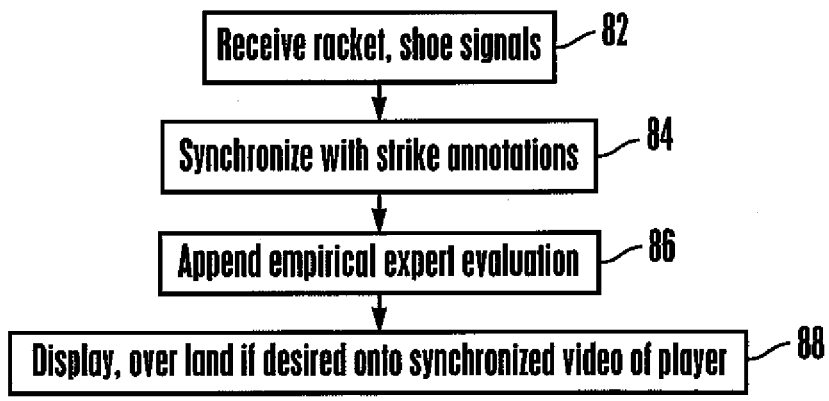
FIG. 4 is a flow chart of example logic according to present principles.

Indeed and now referring to FIG. 4, which shows logic in non-limiting flow chart format that can be executed by any of the processors described above receiving the wireless signals from the racket 44 and shoe 48, at block 82 the signals are received. At block 84 the shoe signals are synchronized with the signals from the racket indicating a strike, with the times of strike being annotated. If desired, empirically-derived expert evaluations based on the signals may be appended to the data at block 86, and then the data presented, overlaid if desired on a synchronized video replay of the player from whom the signals are derived, at block 88.

In synchronizing the shoe pressure signals with racket-ball strikes at block 84, signals from the strike sensors 44*a* may be used as the sources for annotating when the player hit the ball. In some embodiments, the strike sensors 44*a* may be omitted, and only the pressure sensors 44*b* on the handle used to derive strike indications from sudden if small pressure changes in the player's grip on the handle. For example, a player hitting a backhand may momentarily exert less pressure on the handle due to the ball striking the racket head and urging it away from the hand, whereas a player hitting a forehand may momentarily exert increased pressure on the handle due to the ball striking the racket head and urging it harder against the hand.

Moreover, the same differences in momentary pressure variations may be used as indications of whether a forehand or a backhand was hit at the time of the pressure variation, with a spiked increase in pressure indicating a forehand and a spiked decrease indicating a backhand.

As another alternative to determining which stroke was used, the location of the palm of the hand on the handle can be correlated to signals from the strike sensors 44*a* when the strike sensors 44*a* are used and implemented as, e.g., accelerometers. In this case, when an accelerometer indicates forward motion of the racket and the pressure signals from the handle indicate that the palm is on the back of the handle relative to the direction of forward motion, a forehand is inferred, whereas when an accelerometer indicates forward motion of the racket and the pressure signals from the handle indicate that the palm is on the front of the handle relative to the direction of forward motion, a backhand is inferred.

Yet again, the handle sensors 44*b* may be omitted and only the strike sensors 44*a* used. In this case, the strike sensors as discussed above can indicate moments in time when a ball was struck, and also motion of the racket. Prior to presentation as divulged below, a user can be prompted to indicate which hand he uses in playing tennis. Then, signals from the strike sensors 44*a* are indicating a clockwise arc of forward motion are interpreted as a backhand for a right handed player and a forehand for a left handed player, while signals from the strike sensors 44*a* are indicating a counterclockwise arc of forward motion are interpreted as a forehand for a right handed player and a backhand for a left handed player. In any case, it will readily be appreciated that the racket signals may be used to determine both when a strike occurred and whether the shot was a forehand or a backhand.

In appending empirical expert evaluations to the data at block 86, pressure patterns as indicated by the shoe sensors 68, 70, 72, 74 versus ball strikes as indicated by the racket sensor(s) 44*a*, 44*b* can be mapped using expert input to subjective commentary such as "good footwork for a forehand—weight on balls of feet" or "poor form—back on your heels—need to lean in to backhands". The mapping can be stored and then superimposed on the presentation, as disclosed for example below.

Figure 5:
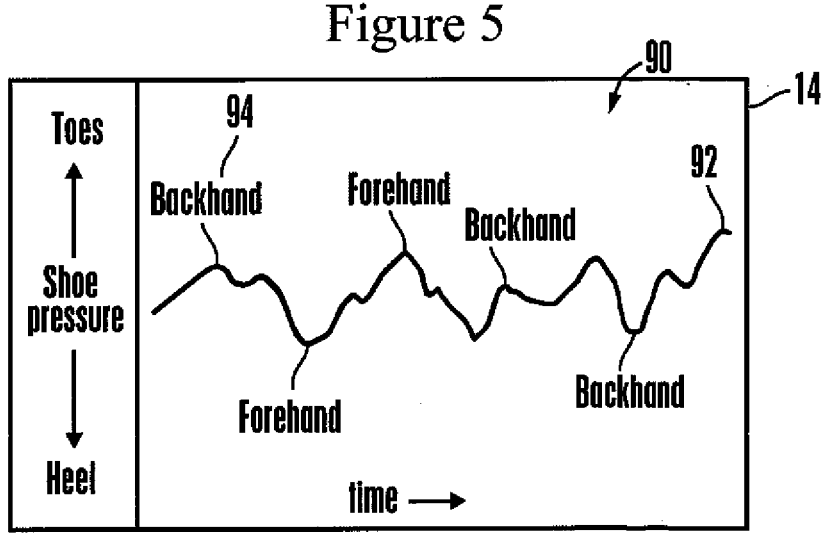
FIGS. 5-7 are screen charts of example indications according to present principles.

FIG. 5 shows a presentation 90 that may be presented on, for example, the display 14 of the CE device 12. In this example, a timeline 92 of shoe pressure is shown, with greater pressure from the toe sensors 68 than the heel sensors 70 indicated by greater timeline magnitude on the y-axis and less pressure from the toe sensors 68 than from the heel sensors 70 indicated by less magnitude on y-axis and with time increasing left along the x-axis. Similar principles can apply to show variances in pronation/supination, e.g., using 3D graphics with supination/pronation indicated in the z-axis. As shown, the timeline of pressure from the shoe sensors has been synchronized with strike annotations 94 derived from the handle sensors. While the annotations 94 in FIG. 5 indicate the type of stroke, in simpler embodiments the annotations may simply indicate "stroke" or "ball strike" or other indication.

Figure 6:
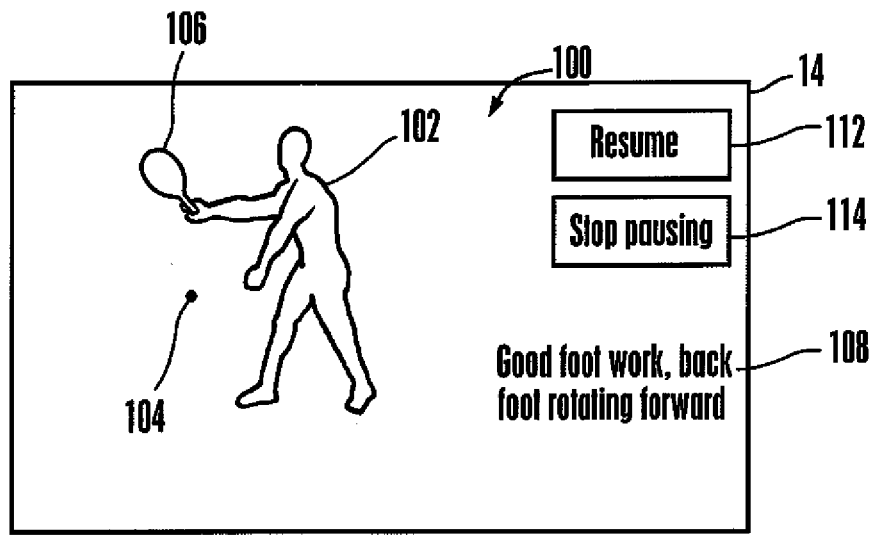

FIG. 6 illustrates a more sophisticated presentation 100 showing recorded video of the player 102, in the example shown, a right handed player in the act of hitting a tennis ball 104 using a backhand stroke with a sports racket 106. An expert evaluation including a comment or message 108 appears on screen based on the shoe signals. In the example shown, the message "back foot rotating forward" is derived from pressure signals indicating supination-to-pronation pressure on the rear shoe, with the subject "good work" being obtained in one example by accessing a table or other data structure using rear foot, supination-to-pronation, and backhand as entering arguments and correlating them to an expert subject comment associated with that particular combination. The timeline of FIG. 5 may be overlaid on the presentation of FIG. 6 if desired.

Figure 7:
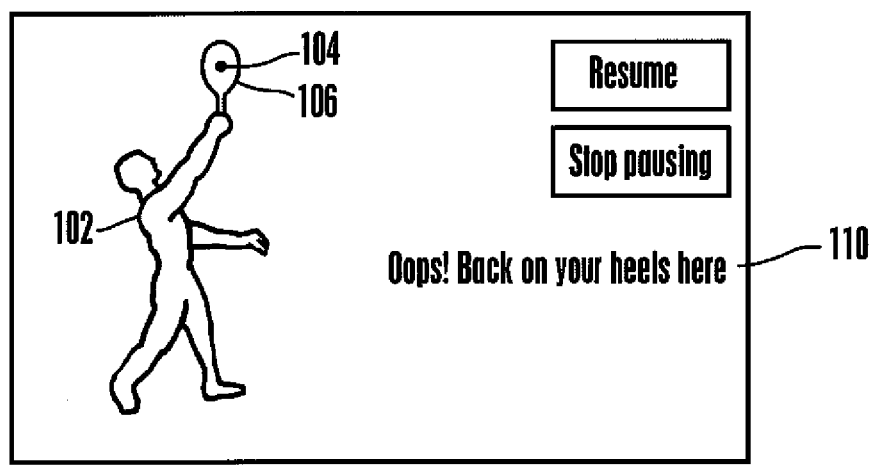

In contrast, FIG. 7 shows a later segment of the video in which the heel pressure sensors from the shoes indicated inordinately great pressure during the stroke. A message 110 reflects as much.

If desired, during video playback, at each stroke the video can automatically pause as the comments 108, 110 are presented, so the player can study a still image at a critical juncture in his game. Video play can be resumed by selecting a "resume" selector 112. If the player desires he can stop further pausing of playback at ball strike moments by selecting a pausing selector 114, which can be toggled to turn pausing on and off.

While the disclosure above refers to a single sports shoe 48, it is to be appreciated that present principles apply to synchronizing the above signals with the signals from the second shoe as well. While the above presentations are shown as video presentations, it is to be understood that they could be audio as well and, for example, the expert evaluations of footwork during a particular stroke be delivered in real time over a wireless link to, e.g., the player's headphones 46 for audible presentation of the evaluation to the player in near-real time, for instance, shortly after the stroke being evaluated and prior to the next stroke.

While the particular COMBINING SIGNAL INFORMATION FROM SHOES AND SPORTS RACKET is herein shown and described in detail, it is to be understood that the subject matter which is encompassed by the present invention is limited only by the claims.

What is claimed is:

1. A device comprising:
   at least one computer memory that is not a transitory signal and that comprises instructions executable by at least one processor for:
   receiving first signals from at least one sensor on a sports racket;
   receiving second signals from at least one sensor on a shoe worn by a player wielding the sports racket; and
   based at least in part on the first and second signals, presenting an indication on at least one display, the indication including indications of whether a forehand or a backhand was hit based on a time of variation in the first signals, with a forehand being indicated responsive to an increase in pressure as indicated by the first signals and with a backhand being indicated responsive to a decrease in pressure as indicated by the first signals.

2. The device of claim 1, wherein the indication is audible.

3. The device of claim 1, wherein the indication is video.

4. The device of claim 1, wherein the instructions are executable for:
   determining the player struck an object with the racket based at least in part on signals from at least one strike sensor on the racket.

5. The device of claim 1, wherein the instructions are executable for:
   determining the player struck an object with the racket based at least in part on signals from at least one pressure sensor on a handle of the racket.

6. The device of claim 1, wherein the instructions are executable for:
   determining from signals from at least one motion sensor on the racket whether the racket has been swung in clockwise or counterclockwise arc.

7. The device of claim 1, wherein the indication includes at least one expert evaluation.

8. The device of claim 1, wherein the indication includes at least one timeline of shoe pressure.

9. The device of claim 1, wherein the indication includes video of the player synchronized with at least one comment derived from the first and second signals.

10. Method comprising:
    correlating first wireless signals from a sports racket with second wireless signals from shoes worn by a player wielding the racket to render footwork indication along with contemporaneous racket motion indication; and
    presenting the indications to allow the player to gain insight into the player's performance,
    wherein the racket motion indication includes backhand or forehand stroke, forehand stroke being output response to a determination that an accelerometer indicates forward motion of the sports racket and pressure signals from a handle of the sports racket indicate pressure on a back of the handle relative to a direction of forward motion of the sports racket, backhand stroke being output response to a determination that an accelerometer indicates forward motion of the sports racket and pressure signals from a handle of the sports racket indicate pressure on a front of the handle relative to a direction of forward motion of the sports racket.

11. The method of claim 10, wherein at least one of: the footwork indication, racket motion indication, is audible.

12. The method of claim 10, wherein at least one of: the footwork indication, racket motion indication, is video.

13. The method of claim 10, comprising:
    determining a player struck an object with the racket based at least in part on signals from at least one strike sensor on the racket.

14. The method of claim 10, comprising:
    determining a player struck an object with the racket based at least in part on signals from at least one pressure sensor on a handle of the racket.

15. The method of claim 10, comprising:
    determining from signals from at least one motion sensor on the racket whether a racket has been swung in clockwise or counterclockwise arc.

16. The method of claim 10, wherein at least one of: the footwork indication, racket motion indication, includes at least one expert evaluation.

17. The method of claim 10, wherein at least one of: the footwork indication, racket motion indication, includes at least one video of the player synchronized with at least one comment derived from the first and second wireless signals.

* * * * *